United States Patent [19]

Bonfield et al.

[11] 4,323,706
[45] Apr. 6, 1982

[54] PRODUCTION OF ACETALDEHYDE OXIME

[75] Inventors: John H. Bonfield, Basking Ridge; Stephen E. Belsky, Parsippany; Donald Pickens, Mendham, all of N.J.

[73] Assignee: Allied Corporation, Morris Township, Morris County, N.J.

[21] Appl. No.: 217,938

[22] Filed: Dec. 18, 1980

Related U.S. Application Data

[63] Continuation of Ser. No. 880,672, Feb. 23, 1978, abandoned.

[51] Int. Cl.$^3$ ............................................. C07C 131/00
[52] U.S. Cl. .................................. 564/253; 564/259; 564/264; 203/77
[58] Field of Search ..................... 564/259, 264, 253

[56] References Cited

U.S. PATENT DOCUMENTS 3,535,361  10/1970  Anders et al. .
3,574,736  4/1971  Fuchs .
3,658,689  4/1973  Steinmetz et al. .
3,752,841  8/1973  Fuchs .

FOREIGN PATENT DOCUMENTS 7017568  6/1972  Netherlands .

OTHER PUBLICATIONS

Weissberger, *Technique of Organic Chemistry*, vol. IV (1965) 478–495.
Brown, Unit Operations (1953) 393–394.

*Primary Examiner*—Bernard Helfin
*Attorney, Agent, or Firm*—Alan M. Doernberg; J. P. Friedenson

[57] ABSTRACT

Acetaldehyde oxime, a commercially useful intermediate in the production of pesticides, is prepared by oximating acetaldehyde with an aqueous hydroxylamine-containing solution to form an aqueous oximation reaction mixture and recovering acetaldehyde oxime from the aqueous oximation reaction mixture by distilling a mixture of acetaldehyde oxime and water directly from the aqueous oximation reaction mixture.

11 Claims, No Drawings

PRODUCTION OF ACETALDEHYDE OXIME

This is a continuation of application Ser. No. 880,672, filed Feb. 23, 1978 and now abandoned.

BACKGROUND OF THE INVENTION

Oximes are conventionally prepared by oximating a ketone or aldehyde with an aqueous hydroxylamine-containing solution. The oxime is then recovered from the aqueous solution for further reaction, as by the halogenation processes described in U.S. Pat. Nos. 3,535,361, 3,574,536, 3,658,869 and 3,751,841. Many oximes are easily recovered from the aqueous oximation reaction mixtures because the relatively water-insoluble oxime forms a separate phase from the aqueous phase, and may be separated by decantation or the like.

Acetaldehyde oxime, also known as acetaldoxime, an important intermediate in the production of certain pesticides, cannot easily be recovered from the aqueous reaction mixture by phase separation because it is relatively water-soluble under most relevant conditions; and, when a separate layer forms containing acetaldehyde oxime, such separate layer also contains appreciable amounts of water and water-soluble impurities. One method of recovering acetaldehyde oxime from the aqueous oximation reaction mixture involves extraction with an organic solvent such as benzene. Such a method is relatively energy and capital expensive, however, because the benzene must then be distilled from the acetaldehyde oxime.

It should be appreciated that many of the known processes for further reacting oximes, and especially acetaldehyde oxime, require a dilute solution of the oxime in water or some other solvent. This is especially true for the chlorination of acetyl aldoxime with $Cl_2$.

SUMMARY OF THE INVENTION

Acetaldehyde oxime is prepared by oximating acetaldehyde with an aqueous hydroxylamine-containing solution to form an aqueous oximation reaction mixture which includes a salt and recovering acetaldehyde oxime from the aqueous oximation reaction mixture by distilling a mixture of acetaldehyde oxime and water directly from the aqueous oximation reaction mixture. The existence of an azeotrope between water and acetaldehyde oxime enables all the acetaldehyde oxime to distill out of the aqueous oximation reaction mixture without large amounts of excess water being distilled, which could undesirably concentrate acetaldehyde oxime in the bottoms of the distillation, leading to product decomposition or side reaction.

The recovered mixture containing acetaldehyde oxime and water and lites including acetaldehyde and ammonia is then purified by a second or lights distillation to remove the lights including acetaldehyde and water and produce a product mixture of acetaldehyde oxime and water relatively free of lights. This product mixture may then be diluted and reacted with $Cl_2$.

DETAILED DESCRIPTION OF THE INVENTION

The present invention includes a method of removing acetaldehyde oxime from an aqueous oximation reaction mixture by distillation as a mixture of acetaldehyde oxime and water. The effectiveness of this distillation is based upon the formation of a minimum-boiling azeotrope between acetaldehyde oxime and water with a composition about 52.5 weight % acetaldehyde oxime and 47.5 weight % water and a boiling point at atmospheric pressure about 95.5° C. In the absence of an azeotrope, one would expect water (boiling point 100° C.) to come off before acetaldehyde oxime (boiling point 114°–115° C.).

Furthermore, in distilling the mixture of acetaldehyde oxime and water from an aqueous oximation reaction mixture, the presence of salt materials such as ammonium sulfate in the reaction mixture favors the rejection of acetaldehyde oxime to the vapor phase. For example, a binary solution of about 5 weight % acetaldehyde oxime is about 95 weight % water may be in equilibrium with only about 17 weight % acetaldehyde oxime in the vapor phase (at 99° C.), while a ternary system of about 5% acetaldehyde oxime, 34% ammonium sulfate and 61% water will be in equilibrium with 46 weight % acetaldehyde oxime in the vapor phase. In fact, the distillation of this mixture from such a ternary composition will result in substantially all of the acetaldehyde oxime being distilled off as a mixture with water near the azeotropic composition of 52.5 weight percent with most of the water remaining in the liquid phase.

The present invention can be practiced whenever acetaldehyde oxime is produced in an aqueous oximation reaction mixture, but is preferably practiced when the reaction mixture includes an ammonium salt, as especially when it includes ammonium sulfate. The remaining solution after distillation is substantially free of organic materials and can be utilized for fertilization or the like, preferably after evaporative crystallization of the ammonium salt as is conventional. The preferred reaction mixture is one in which the hydroxylamine-containing solution includes hydroxylamine sulfate, sulfuric acid and ammonium sulfate, which may be produced by the conventional Raschig process, to which a base is added to generate hydroxylamine for oximation of acetaldehyde. The preferred base is ammonia, as is conventionally used in oximation processes. The additional ammonium sulfate thus produced tends to increase the acetaldehyde oxime concentration of the vapor and distillation (as shown in the present invention) and the recoverable ammonium sulfate for fertilizer use (as in conventional).

The present invention is not, however, limited to ammonium sulfate-producing oximating reagents but may be practiced with any aqueous hydroxylamine-containing reagent of the type known to the art.

In general, the aqueous oximation reaction mixture contains after reaction between about 1 and about 10 weight percent acetaldehyde oxime, between about 40 and about 90 weight % water and the remainder being salts such as ammonium sulfate and small amounts of ammonium nitrate, free bases such as ammonia and minor organic impurities such as unreacted acetaldehyde and residue.

The aqueous oximation reaction mixture from which distillation occurs may be in one or two phases. With water, acetaldehyde oxime and ammonium sulfate, the existence of a two phase system occurs in a relatively narrow range within the broader range of about 30–60% water, about 0–45% ammonium sulfate and about 2–70% acetyl aldoxime. The presence of acetaldehyde as an impurity broadens the two phase range somewhat. Distillation from the two phase system is one preferred mode, even though the two phases may disappear once an appreciable amount of acetaldehyde oxime has been distilled off. In the present invention the mixture of acetaldehyde oxime and water is distilled directly from the aqueous oximation reaction mixture rather than from a more refined solution from which the water-soluble materials (such as ammonium sulfate) have been removed. Lights (also called lites) distillation to remove lower boiling impurities such as acetaldehyde and ammonia is conducted on the mixture of acetaldehyde oxime and water after is has been distilled from the aqueous oximation reaction mixture.

Lites distillation from the aqueous oximation reaction mixture before distillation of the acetaldehyde oxime-water mixture is disadvantageous because the concentration of acetaldehyde in the distillate remains at a high level (about 1–3%) falling only slightly. This phenomena is believed to result from the slight decomposition of ammonium sulfate to free ammonia and ammonium acid sulfate and the tendency of ammonium acid sulfate to decompose acetaldehyde oxime to free ammonia and acetaldehyde and other side products. Distilling the overheads from the first distillation (for example 50% acetaldehyde oxime with 2.3% acetaldehyde and 0.6% ammonia in 1750 ml of overheads) produces 4.5%, 2.2% and 1.5% acetaldehyde in the first three 50 ml aliquots and 7.4%, 4.1% and 2.4% ammonia in the first three aliquots. The remaining 1600 ml of overheads from the main distillation contains about 0.78% acetaldehyde (down from 2.3%) and 0.1% ammonia (down from 0.6%), both by weight of acetaldehyde oxime. The overheads from lites distillation may be recycled to the oximation reaction mixture. This lites distillation may occur at 80°–96° C. for example, with the above data taken from a 20 plate 1:1 reflux ratio batch distillation. Byproducts acetonitrile and alcohol will also preferentially accumulate in the lites overhead.

The oximation reaction itself is performed in a convention fashion at atmospheric pressure with the temperature at the point where acetaldehyde is added preferably kept below about 50° C. and more preferably between 20° C. and 35° C. Once the acetaldehyde is added to the aqueous hydroxylamine containing mixtures of hydroxylamine sulfate and ammonium sulfate, the base (ammonia) is then added, preferably below about 70° C. and more preferably between about 20° and about 35° C. In a continuous process, acetaldehyde and base may be added simultaneously.

The product mixture of water and acetaldehyde after lites distillation may be of whatever purity is desired, based on the extent of lites distillation. Purity of less than 1.2% acetaldehyde and less than 0.25% ammonia, based on weight of acetaldehyde oxime, which impurity levels are most suitable for subsequent chlorination, are easily obtained with a relatively small degree of lites distillation.

EXAMPLE 1—DEMONSTRATION OF AZEOTROPE

Distillations were conducted using the standard Othmer Still technique of the system of acetaldehyde oxime and water with the following values determined: boiling point as a function of the weight fraction acetaldehyde oxime in the binary solution, mol fraction of acetaldehyde oxime in vapor phase as fraction of mol fraction of acetaldehyde oxime in the liquid phase and weight percent and boiling temperature of the azeotrope at pressures from 50–1500 mm Hg absolute. Each of these tests confirmed the existence of an azeotrope at 52.5 weight % acetaldehyde oxime at 95.5° C. at 760 mm Hg absolute, whose composition is reduced about 1% acetaldehyde oxime for each 100 mm Hg reduction in pressure.

EXAMPLE 2—TERNARY SYSTEM OF AMMONIUM SULFATE, ACETALDEHYDE OXIME AND WATER

The vapor-liquid equilibrium was determined for mixtures of ammonium sulfate, acetyl aldoxime and water at equilibrium at 760 mm Hg absolute. No appreciable ammonia nor any ammonium salt was present in the vapor phase. Standard Othmer Still methods were used to distill acetaldehyde oxime (AAO) and water from a ternary mixture with ammonium sulfate (AS) and the acetaldehyde oxime concentrations determined by gas chromatography. Data are displayed in Table 1.

TABLE 1

VAPOR-LIQUID EQUILIBRIUM - ACETALDEHYDE OXIME
WATER OVER ACETALDEHYDE OXIME - WATER AMMONIUM SULFATE

| Liquid Weight % | | | Vapor | |
|---|---|---|---|---|
| Ammonium Sulfate | Wt. % AAO AS Free | Acetaldehyde Oxime | Temp. °C. | Wt. % AAO |
| 33.7 | 7.7 | 5.15 | 96.7 | 46 |
| 34.6 | 6.06 | 4.01 | 97.0 | 41.5 |
| 35.3 | 4.38 | 2.78 | 97.5 | 37 |
| 37.0 | 2.99 | 1.88 | 98.0 | 29 |
| 38.5 | 1.99 | 1.23 | 99.0 | 19.5 |
| 40.3 | 1.19 | .71 | 99.0 | 14.5 |
| 42.0 | .74 | .43 | 100.0 | 8.0 |

The balance up to 100% in the liquid and vapor phase was water (except for about 1–3% impurities in the vapor phase including ammonia).

EXAMPLE 3—DISTILLATION PROCESS

A reboiler was charged with 185 grams ammonium sulfate, 315 grams water, 100 grams of about 55 weight % acetaldehyde oxime (55.5 grams) in water also containing 0.64% acetaldehyde and 0.22% ammonium by weight of acetaldehyde oxime. At a 10:1 rectification to forward ratio, 15 ml aliquots of forward material was analyzed as shown in Table 2.

TABLE 2

| | | ANALYSIS 15 ml Aliquots O/H | | |
|---|---|---|---|---|
| Time Min. | Overhead °C. | Acetaldehyde % vol. Acetaldehyde Oxime | Weight % Acetaldehyde Oxime | pH Reboiler |
| 0 | 93° | at initial boil up | | 7.6 |
| 25 | 94.5 | 5.25 | 45.7 | 5.6 |
| 45 | 94.5 | 3.4 | 54.3 | 5.5 |
| 70 | 95 | 2.85 | 53.2 | 5.45 |
| 95 | 95 | 2.45 | 54.2 | 4.4 |
| 120 | 95 | 2.0 | 55.5 | 4.1 |
| 140 | 95.5 | 1.7 | 55.5 | 3.95 |
| 165 | 96 | 1.55 | 51 | 3.85 |
| 190 | 96–100 | 1.15 | 35.1 | 3.8 |

It should be appreciated that acetaldehyde oxime was present at only 9.25% of the total original charge or at about 55/415 or about 13.2% based on weight of acetaldehyde oxime and water. Acetaldehyde oxime is present at 45–55.5% in the mixture obtained by distillation until the final period when the temperature was permitted to rise to 100° C.

EXAMPLE 4—DISTILLATION ON TOTAL REFLUX

Example 3 was repeated with total reflux at 93°-94° C. and only small samples removed from the reflux for analysis. The proportion of lower boiling acetaldehyde by weight acetaldehyde oxime remained below about 5.5% in the reflux (as measured by gas chromatography) indicating no appreciable decomposition of acetaldehyde oxime to acetaldehyde.

EXAMPLE 5—CONTINUOUS FEED

Example 3 was repeated with continuous feed and a three hour average residence time, with the overhead composition at 106° C. distillation and a 95° C. reboiler heads temperature. The overheads stabilized at 34–35% acetaldehyde oxime and the following impurity proportions by weight of acetaldehyde oxime: 1.8% acetaldehyde and 0.66% ammonia.

It appears from Example 5 that the decomposition of ammonium sulfate under distillation conditions to ammonia gas and sulfuric acid lowers the pH of the solution no further than to 3.8 (neutral pH for this mixture would be 5.5) and that such a drop results in no more than 3 weight % acetaldehyde (from product decomposition) relative to acetaldehyde oxime.

EXAMPLE 6—BATCH REACTION AND DISTILLATION

A mixture of 12800 grams of Rashig hydrox solution containing:

| | |
|---|---|
| $NH_4NO_3$ | 171 grams |
| $H_2SO_4$ | 1097 grams |
| $(NH_4)_2SO_4$ | 2552 grams |
| $(NH_2OH)_2H_2SO_4$ | 7590 grams | was mixed with 700 grams acetaldehyde (which would stoichiometrically produce 940 grams acetaldehyde oxime) and an aqueous solution of 6 weight % acetaldehyde oxime (80 grams acetaldehyde oxime) to simulate a recycle of the terminal distillation fraction. The mixture was neutralized with 670 grams of ammonia to a pH of 5.5 and then distilled with a 25 plate Oldershaw column at 2:1 reflux to forward ratio. Twenty 250 ml fractions were taken off and analyzed for acetaldehyde oxime by a refractive index method. The first seven fractions contained 50% acetaldehyde oxime and could constitute the "main" or product fraction of the distillate (containing 960 grams acetaldehyde oxime). The next seven 25 ml fractions contained a declining acetaldehyde oxime proportion averaging 5-6% acetaldehyde oxime and could constitute the terminal or recycle fraction (containing 7 grams acetoxime). Subsequent 250 ml fractions contained no measurable acetaldehyde oxime and thus need not be subjected to any purification for oxime before ammonium sulfate recovery.

When this example was repeated with multiple recycles of the terminal fraction, the acetaldehyde oxime continued to come off at 90-93% of theoretical yield in a mixture of about 50% acetaldehyde oxime and about 50% water. Even the addition of extra water during recycle had no effect on the product recovery.

When the distillation of this example was repeated by distilling acetaldehyde oxime from a binary system of water and acetyl aldoxime, the acetaldehyde oxime fell from about 45 weight % in the first 250 ml fraction continuously to about 5 weight % in the twentieth fraction.

EXAMPLE 7—CONTINUOUS REACTION AND DISTILLATION

The feeds shown in Table 3 (in grams per hour) were made to a microreactor of 250 ml to overflow. Reaction product was fed to a stripping column of 25 plates with 8 inch protruded metal packing with variable reflux return control.

TABLE 3

| 41° C. - BATCH MIX REACTOR | |
|---|---|
| Component | Amount Fed |
| Acetaldehyde | 380 grams (ml) of 25% solution in water at a rate of 180 ml/hour (or 95 grams acetaldehyde total) |
| Hydrox Solution | 1601 grams (1275 ml) having 10.7% hydroxylamine by weight as $(NH_2OH)_2H_2SO_4$ |
| Ammonia | 84 grams |

The main cut of distillate (293.5 grams) was determined to contain 43 weight % acetaldehyde oxime by refractive index and 43.5 weight % acetaldehyde oxime by gas liquid chromatography. It also contained as impurities 2.35% acetaldehyde and 1.05% ammonia. In the still bottoms were predominantly ammonium sulfate with a pH of 3.95, about 0.45% excess hydroxylamine and no detectable acetaldehyde oxime. Using an intermediate value of 43.25% acetaldehyde oxime for the "main cut", it could be computed to contain 126.94 grams of acetaldehyde oxime, or 99.8% of theoretical yield.

When this example was repeated in a five hour run, using 880 grams of 25% acetaldehyde oxime and 3770 grams of Raschig hydrox, essentially theoretical yield was obtained in a 608 gram "main cut" at 48.8–50 weight % with only 1.1% acetaldehyde and 2.0% ammonia. The sulfate bottoms had less than 0.02% acetaldehyde oxime and about 0.74% hydroxylamine.

We claim:

1. A method for preparing acetaldehyde oxime by oximating acetaldehyde with an aqueous oximation reaction mixture which includes a salt and recovering acetaldehyde oxime from the aqueous oximation reaction mixture, characterized in that the acetaldehyde oxime is recovered by:

first distilling a mixture of acetaldehyde oxime, water and lights including acetaldehyde and ammonia directly from the aqueous oximation reaction mixture under conditions of temperature and pressure at which acetaldehyde oxime, water and lights are volatile, and then distilling lights from said mixture of acetaldehyde oxime, water and lights under conditions of temperature and pressure at which lights are volatile and acetaldehyde oxime is nonvolatile to remove the lights and produce a product mixture of acetaldehyde oxime and water relatively free of lights.

2. The method of claim 1 wherein the first distillation is conducted between about 95.5° C. and about 110° C.

3. The method of claim 2 wherein the first distillation is conducted between about 96° C. and about 100° C.

4. The method claim 1 wherein the aqueous oximation reaction mixture includes an ammonium salt.

5. The method of claim 4 wherein the aqueous oximation reaction mixture includes ammonium sulfate.

6. The method of claim 1 wherein the aqueous hydroxylamine-containing solution includes hydroxylamine sulfate, sulfuric acid and ammonium sulfate, and a base is added to the aqueous oximation reaction mixture.

7. The method of claim 6 wherein the base is ammonia.

8. The method of claim 1 wherein the product mixture is reacted with $Cl_2$.

9. The method of claim 8 wherein the product mixture is diluted with water to between about 1% and about 25% acetaldehyde oxime by weight of diluted solution before reaction with $Cl_2$.

10. The method of claim 9 wherein the dilute solution contains between about 10 and about 20 weight percent acetaldehyde oxime.

11. The method of claim 1 wherein the lights are distilled under conditions reducing the acetaldehyde content of the product mixture to less than 1.2% and the ammonia content of the product mixture to less than 0.25%, based on weight of acetaldehyde oxime.

* * * * *